US008215171B1

(12) United States Patent (10) Patent No.: US 8,215,171 B1
Smith et al. (45) Date of Patent: Jul. 10, 2012

(54) UNIFORM MASS SENSITIVITY THICKNESS SHEAR MODE QUARTZ RESONATOR

(75) Inventors: Allan Smith, Chatham, MA (US);
Charity F. Smith, legal representative, Chatham, MA (US); Venkat R. Bhethanabotla, Tampa, FL (US);
Anthony J. Richardson, Palmetto, FL (US)

(73) Assignee: University of South Florida, Tampa, FL (US)

( * ) Notice: Subject to any disclaimer, the term of this patent is extended or adjusted under 35 U.S.C. 154(b) by 318 days.

(21) Appl. No.: 12/547,976

(22) Filed: Aug. 26, 2009

Related U.S. Application Data

(60) Provisional application No. 61/091,903, filed on Aug. 26, 2008.

(51) Int. Cl.
*G01N 29/036* (2006.01)
*H01L 41/00* (2006.01)
(52) U.S. Cl. .................................... 73/580; 310/313 R
(58) Field of Classification Search .................... 73/580, 73/61.45, 54.16, 54.42; 374/16, 45; 310/311, 310/312, 313 R
See application file for complete search history.

(56) References Cited

U.S. PATENT DOCUMENTS

| | | | | | |
|---|---|---|---|---|---|
| 5,661,233 | A | * | 8/1997 | Spates et al. | 73/61.45 |
| 5,705,399 | A | * | 1/1998 | Larue | 436/501 |
| 5,852,229 | A | * | 12/1998 | Josse et al. | 73/24.06 |
| 6,546,820 | B1 | * | 4/2003 | Van et al. | 73/865.8 |
| 7,159,463 | B2 | * | 1/2007 | Dayagi et al. | 73/579 |
| 7,568,377 | B2 | * | 8/2009 | Bhethanabotla et al. | 73/24.06 |
| 7,681,433 | B2 | * | 3/2010 | Konno et al. | 73/24.06 |
| 7,995,008 | B2 | * | 8/2011 | Miwa | 345/76 |
| 2007/0251321 | A1 | * | 11/2007 | Fritze et al. | 73/579 |

OTHER PUBLICATIONS

Bulk Acoustic wave sensors for sensing measurand-Induced electrical property changes in solutions, Zhang 2t al. , May 2001.*
Mecea, Loaded Vibrating Quartz Sensors, Sensors and Actuators A Phys, 1994, vol. 40, pp. 1-27.
Ballantine, et al., Acoustic Wave Sensors and Responses, Acoustic Wave Sensors; Theory, Design, and Physico-Chemical Applications, 1997, Academic Press, San Diego, CA, pp. 36-68.
Sauerbrey, Verwendung Von Schwingquarzen Zur Wagung Dunner Schichten Und Zur Mikrowagung, Zeitschrift Fur Physik, 1959, vol. 155, pp. 206-222.
Mecea, A New Method of Measuring the Mass Sensitive Areas of Quartz Crystal Resonators, J. Phys. E. Sci. Instrum., 1989, vol. 22, pp. 59-61.
Mueller, et al., Direct Gravimetric Calibration of a Quartz Crystal Microbalance, The Review of Scientific Instruments, 1968, vol. 39, No. 3, pp. 291-295.

(Continued)

*Primary Examiner* — J M Saint Surin
(74) *Attorney, Agent, or Firm* — Robert Varkonyi; Smith & Hopen, P.A.

(57) ABSTRACT

A ring electrode design that produces a uniform mass sensitivity distribution across a TSM device is presented. A new technique and apparatus to measure this mass sensitivity distribution is also presented. Novel electrode geometries on thickness shear mode (TSM) quartz resonators achieve radial uniformity of mass sensitivity, how receptive the device is to mass loadings, and high frequency stability across the active sensing area of the sensor device. The device allows for absolute mass measurement down to the nanogram level. Fabricated devices utilizing model predictions were tested using this apparatus, and good agreement between theory and experiment is found.

20 Claims, 13 Drawing Sheets

OTHER PUBLICATIONS

Martin, et al., Characterization of a Quartz Crystal Microbalance with Simultaneous Mass and Liquid Loading, Analytical Chemistry, 1991, vol. 63, pp. 2272-2281.

Menon, et al., Coated-Quartz Crystal Resonator (QCR) Sensors for On-Line Detection of Organic Contaminants in Water, IEEE Transactions on Ultrasonics, Ferroelectrics, and Frequency Control, 1998, vol. 45, No. 5, pp. 1416-1426.

Smith, Gravimetric Analysis of the Nonvolatile Residue from an Evaporated Droplet, Using the Quartz Crystal Microbalance/Heat Conduction Calorimeter, Journal of ASTM International, 2006, vol. 3, No. 6, pp. 1-5.

Smith, et al., Principles of Quartz Crystal Microbalance/Heat Conduction Calorimetry: Measurement of the Sorption Enthalpy of Hydrogen in Palladium, Thermochimica Acta, 2005, vol. 432, pp. 202-211.

Wang, et al., Perturbation Method for Analyzing Mass Sensitivity of Planar Multilayer Acoustic Sensors, IEEE Transactions on Ultrasonics, Ferroelectrics, and Frequency Control, 1996, vol. 43, No. 5, pp. 844-851.

Cumpson, et al., The Quartz Crystal Microbalance; Radial/Polar Dependence of Mass Sensitivity Both On and Off the Electrodes, Meas. Sci. Technol., 1990, vol. 1, pp. 544-555.

Cumpson, Quartz Crystal Microbalance: A New Design Eliminates Sensitivity Outside the Electrodes, Often Wrongly Attributed to the Electric Fringing Field, J. Vac. Sci. Technol. A, 1997, vol. 15, No. 4, pp. 2407-2412.

Ward, et al., Radial Mass Sensitivity of the Quartz Crystal Microbalance in Liquid Media, Analytical Chemistry, 1991, vol. 63, pp. 886-890.

Wenzel, et al., Analytic Comparison of the Sensitivities of Bulk-Wave, Surface-Wave, and Flexural Plate-Wave Ultrasonic Gravimetric Sensors, Appl. Phys. Lett., 1989, vol. 54, No. 20, pp. 1976-1978.

Josse, et al., Analysis of the Radial Dependence of Mass Sensitivity for Modified-Electrode Quartz Crystal Resonators, Analytical Chemistry, 1998, vol. 70, pp. 237-247.

Ansorge, et al., Plano-Convex Shaped Langasite Microbalances for High Temperature Applications, IEEE Sensors Conference, 2007, pp. 1424-1427.

Lu, et al., Quartz Crystal Microbalance with Rigid Mass Partially Attached on Electrode Surfaces, Sensors and Actuators A, 2004, vol. 112, pp. 203-210.

* cited by examiner

UNIFORM MASS SENSITIVITY THICKNESS SHEAR MODE QUARTZ RESONATOR

CROSS REFERENCE TO RELATED APPLICATION

This application claims priority to currently U.S. Provisional Patent Application No. 61/091,903, entitled "Uniform Mass Sensitivity Thickness Shear Mode Quartz Resonator", filed on Aug. 26, 2008, the contents of which are herein incorporated by reference.

GOVERNMENT SUPPORT STATEMENT

This invention was made with government support under grant numbers ECCS-0801929 and IIP-07122360 awarded by the National Science Foundation. The government has certain rights in the invention.

FIELD OF INVENTION

This invention relates to sensing devices. Specifically, the invention provides a thickness shear mode resonator.

BACKGROUND OF THE INVENTION

Utilization of a thickness shear mode (TSM) quartz resonator as a mass characterization device for minute mass loadings, down to the nanogram level, is well established. Application of TSM resonators as thin-film thickness and density monitors, detectors of chemical compounds and contaminants in gaseous and liquid environments, and biosensors has been extensive over the last two decades (G. Sauerbrey. Z. Phys., vol. 155, pp. 206-222, 1959; R. M. Mueller and W. White, "Direct gravimetric calibration of a quartz crystal microbalance." Rev. Sci. Instr., vol. 39, pp. 291-295, 1968; S. J. Martin, et al., "Characterization of a quartz crystal microbalance with simultaneous mass and liquid loading." Analytical Chemistry, vol. 63, pp. 2272-2281, 1991; A. Menon, et al., "Coated-quartz crystal resonator (QCR) sensors for on-line detection of organic contaminants in water." IEEE Trans. Ultrason., Ferroelect., Freq. Contr., vol. 45, pp. 1416-1426, 1998; A. Smith, "Gravimetric analysis of nonvolatile residue from an evaporated droplet, using the quartz crystal microbalance/heat conduction calorimeter." J. ASTM Intl., vol. 3, pp. 1-5, 2006; A. Smith and H. M. Shirazi, "Principles of quartz crystal microbalance/heat conduction calorimetry: measurement of the sorption enthalpy of hydrogen in palladium." Thermochim. Actua., vol. 432, pp. 202-211, 2005; D. S. Ballantine, Jr., et al., Acoustic Wave Sensors: Theory, Design, and Physico-Chemical Applications. San Diego, Calif. USA: Academic Press, 1997). Typically referred to as a quartz crystal microbalance (QCM), a TSM quartz resonator consists of a quartz disk of the thickness of which depends upon the operating resonance frequency, with metallic planar electrodes deposited on both faces. Typical resonance frequencies are between 5 and 10 MHz (P. J. Cumpson and M. P. Seah, "The quartz crystal microbalance; radial/polar dependence of mass sensitivity both on and off the electrodes." Meas. Sci. Tech., vol. 1, pp. 544-555, 1990; P. J. Cumpson, "Quartz crystal microbalance: A new design eliminates sensitivity outside the electrodes, often wrongly attributed to the electric fringing field." J. Vac. Sci. Tech. A, vol. 15, pp. 2407-2412, 1997), with the resulting mass sensitivities in the nanogram range. All of the devices considered in this study were plano-plano AT-cut quartz Cr/Au electroded resonators having base operating frequencies of 5 MHz.

Deposition of mass, either in the form of a thin mass layer or point mass, that is inertially coupled to the device surface, causes a reduction in the resonance frequency, which is directly proportional to the minute mass deposited. However, an important limitation on the mass sensitivity of current TSM devices exists. Utilization of the Sauerbrey model to directly relate the frequency shift to mass loading requires that the mass be uniformly distributed across the surface plane of the TSM device. While the mass sensitivity distribution is quite non-uniform for typically utilized devices with circular electrodes, the Sauerbrey model agrees with experimental values within a percent or so, for uniformly distributed elastic films. The non-uniformity of mass sensitivity of current TSM devices is well documented (P. J. Cumpson and M. P. Seah, "The quartz crystal microbalance; radial/polar dependence of mass sensitivity both on and off the electrodes." Meas. Sci. Tech., vol. 1, pp. 544-555, 1990; P. J. Cumpson, "Quartz crystal microbalance: A new design eliminates sensitivity outside the electrodes, often wrongly attributed to the electric fringing field." J. Vac. Sci. Tech. A, vol. 15, pp. 2407-2412, 1997; M. D. Ward and E. J. Delawski, "Radial mass sensitivity of the quartz crystal microbalance in liquid media." Analytical Chemistry, vol. 63, pp. 886-890, 1991); V. M. Mecea, "Loaded vibrating quartz sensors." Sens. Actuators A: Phys., vol. 40, pp. 1-27, 1994; F. Josse, et al., "Analysis of the radial dependence of mass sensitivity for modified-electrode quartz resonators." Analytical Chemistry, vol. 70, pp. 237-247, 1998). This non-uniformity devices is well documented, (F. Josse, et al., Analysis of the radial dependence of mass sensitivity for modified-electrode quartz resonators. Analytical Chemistry, 70, pp. 237-247, 1998; P. J. Cumpson, M. P. Seah, The quartz crystal microbalance; radial/polar dependence of mass sensitivity both on and off the electrodes. Meas. Sci. Tech., 1, pp. 544-555, 1990), and is attributed to the reduction in particle displacement amplitude extending from the center. At the device center, the resonating wave drives the quartz from all radial directions prompting maximum displacement and, consequently, mass sensitivity. Moving away from the center, the displacement amplitude tapers off with radial position producing a Gaussian-like distribution in the mass sensitivity P. J. Cumpson, M. P. Seah, The quartz crystal microbalance; radial/polar dependence of mass sensitivity both on and off the electrodes. Meas. Sci. Tech., 1, pp. 544-555, 1990). Further, the current mass sensitivity devices are susceptible to mechanical vibrations prompting instability and inaccuracies in measurements. Additional contributions to the non-uniformity of the mass sensitivity arise from the anisotropic structure of the quartz. Observed deviations in sensitivity measurements from other studies, sweeping multiple radial axes of the resonator from 0=0° to 90°, indicates that the wave propagation characteristics are notably different depending on the axis of motion in the quartz substrate (M. D. Ward and E. J. Delawski, "Radial mass sensitivity of the quartz crystal microbalance in liquid media." Analytical Chemistry, vol. 63, pp. 886-890, 1991).

These deviations may be acceptable for mass measurement and material characterization of uniform films, but current resonator surfaces cannot confine liquid droplets within the area of constant mass sensitivity. Current analytical and mechanical mass balances are inadequate based upon their high costs and low mass sensitivity, limited to microgram measurement.

Although the studies were not explicitly driven towards reducing the effects of the anisotropy of piezoelectric substrates on the wave propagation and mass sensitivity profile, previous research has considered alternative quartz surface geometries including plano-convex, with the top face of the crystal convexly contoured and the bottom remaining planner, to eliminate the destructive coupling observed between the fundamental and flexural (parasitic) oscillating modes in plano-plano devices. For 'n-m' QCR devices, studies have shown that smaller electrodes and thicker electrodes result in more sensitive mass detection, as the larger mass traps the acoustic wave within the electroded region of the quartz crystal. Cancellation of the fundamental operating mode by these flexural modes upon the deposition of electrode mass on the plano-plano resonator device dampens the energy of the resonator prompting a lower quality factor, Q (E. Ansorge, et al., "Plano-convex shaped langasite microbalances for high temperature applications." Proceedings, IEEE Sensors 2007, Atlanta, Ga., USA, 2007). The decoupling of these modes for electroded plano-convex surfaces forces all of the energy of the driving acoustic wave to the center with minimal energy trapping extending out to the crystal edge. As a result, the Q-factor and mass sensitivity is higher, by a factor of two, for the plano-convex resonator compared to the plano-plano (M. D. Ward and E. J. Delawski, "Radial mass sensitivity of the quartz crystal microbalance in liquid media." *Analytical Chemistry*, vol. 63, pp. 886-890, 1991). Reduction of the anisotropic effects would be observed using the plano-convex surface with the concentration of the energy within a small active area at the center of the resonator. However, an increase in Q-factor prompts a narrowing of the mass sensitivity distribution which would make achieving a uniform mass sensitivity distribution potentially difficult. The broad-distribution indicative of the plano-plano quartz resonator is inherently capable of producing the bimodal profile necessary to achieve uniformity over a large sensing area.

SUMMARY OF THE INVENTION

The advent of a TSM resonator with uniform mass sensitivity allows for accurate and inexpensive characterization of mass loadings down to the nanogram scale. The electrode design(s) producing radial uniformity of mass sensitivity within the active sensing area of a thickness shear mode (TSM) quartz resonator is inherent to the field of absolute mass measurement. A TSM device exhibiting both uniform mass sensitivity and high frequency stability results in a robust and efficient mass balance capable of measuring nanogram level mass loadings. The existence of a reliable nanobalance would greatly enhance the field of mass measurement eliminating the reliance on analytical and mechanical balances that are expensive, limited to microgram level mass sensitivity, and are susceptible to mechanical vibrations. Non-uniformity of mass sensitivity is found in typical TSM devices, and is the primary factor influencing the sensitivity profile (F. Josse, et al., "Analysis of the radial dependence of mass sensitivity for modified-electrode quartz resonators." *Analytical Chemistry*, vol. 70, pp. 237-247, 1998). A practical TSM device exhibiting constant mass sensitivity across the active sensing area and high frequency stability will yield a viable robust nanobalance. The existence of a TSM-based nanobalance will enable its utilization in the determination of absolute mass, a shortcoming of current TSM devices. Furthermore, a working device would eliminate the dependence on mechanical and analytical mass balances which are expensive, limited to microgram level mass sensitivity, and suffer considerably from mechanical vibrations. Processes involving gravimetric measurements such as the determination of non-volatile residue (NVR) contamination in high-purity solvents would benefit significantly with the advent of a nanobalance (A. Smith, "Gravimetric analysis of non-volatile residue from an evaporated droplet, using the quartz crystal microbalance/heat conduction calorimeter." *J. ASTM Intl.*, vol. 3, pp. 1-5, 2006; A. Smith and H. M. Shirazi, "Principles of quartz crystal microbalance/heat conduction calorimetry: measurement of the sorption enthalpy of hydrogen in palladium." *Thermochim. Actua.*, vol. 432, pp. 202-211, 2005). A current method to characterize NVR per volume of solvent involves a thermal gravimetric technique where a large quantity of solvent is evaporated and the remnant NVR weighed. This process is both expensive and time consuming.

The invention involves the modification of the electrode configurations of TSM resonator devices to achieve radial uniformity of mass sensitivity and high frequency stability to produce an absolute mass balance capable of accurately measuring mass down to the nanogram scale. Presented below are prognostic and experimental analyses of mass sensitivity distributions for a ring electrode configuration having an inner and outer diameter of 4 and 10 mm, respectively, and a model driven Au/Cr electrode thickness predicted to produce a uniform mass sensitivity. Additionally, descriptions of the fabrication of the TSM devices and a novel experimental apparatus constructed to measure mass sensitivity are presented.

The present device eliminates the non-uniformity of mass sensitivity of commercially available devices through modification of the electrode design, the primary factor influencing the sensitivity profile (F. Josse, et al., Analysis of the radial dependence of mass sensitivity for modified-electrode quartz resonators. *Analytical Chemistry*, 70, pp. 237-247, 1998). A tangible TSM device exhibiting constant mass sensitivity across the active sensing area and high frequency stability will yield a viable robust nanobalance.

Available mathematical modeling of the radial mass sensitivity distributions for simple electrode designs, namely solid 'n-m' and ring configurations (FIG. 1 depicts these two cases) is an efficient and valuable tool to analyze designs producing a uniform mass sensitivity distribution. A model driven Cr/Au electrode thickness predicted to produce a uniform mass sensitivity was used. Additionally, descriptions of the fabrication of the TSM devices and a novel experimental apparatus constructed to measure mass sensitivity distribution are presented.

Modification of the electrode configurations of TSM resonator devices exhibited radial uniformity of mass sensitivity and high frequency stability to produce an absolute mass balance capable of accurately measuring mass down to the nanogram scale. As such, disclosed herein is a sensing device with a series of electrodes on the first and second faces of a piezoelectric resonating material. In some embodiments, the piezoelectric resonating material is AT-cut quartz, and may have an operating frequency of 5 MHz or 11 MHz in specific embodiments. The first electrode, disposed on the upper face, has a ring geometry further comprising an inner ring diameter of 4 mm and an outer ring diameter of 10 mm. The second electrode, disposed on the bottom face, has a circular geometry further comprising an outer diameter of at least 10 mm. A polymeric layer is covering at least a portion of the first electrode. The electrodes are optionally comprised of chromium adhesion and gold layers. In specific embodiments of the invention, the chromium adhesion layer is about 75 angstroms and the gold layer is about 1050 angstroms. The sensing device may also have an alkanethiol self assembled monolayer disposed on the first face of the piezoelectric resonating material.

Also disclosed is a sensing device utilizing a nanobalance/calorimeter, having a calorimeter body, a heat sink in thermal communication with the calorimeter body, and at least one input on the calorimeter body. The TSM sensing device, described above, is mounted in the calorimeter body, for detecting mass. The sensing device optionally includes at least a micropositioner, an oscillator circuit, or a humidity controller. The nanobalance/calorimeter may also include an inert gas source, in fluid communication with the calorimeter such that the inert gas source may be injected into the calorimeter.

In specific embodiments of the invention, the TSM sensing device is thermally coupled to a heat sink through a Peltier thermocouple plate. The calorimeter is optionally adapted to operate between ambient temperature and 100° C., and may also include channels drilled in the body, adapted to permit water circulation throughout the body.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
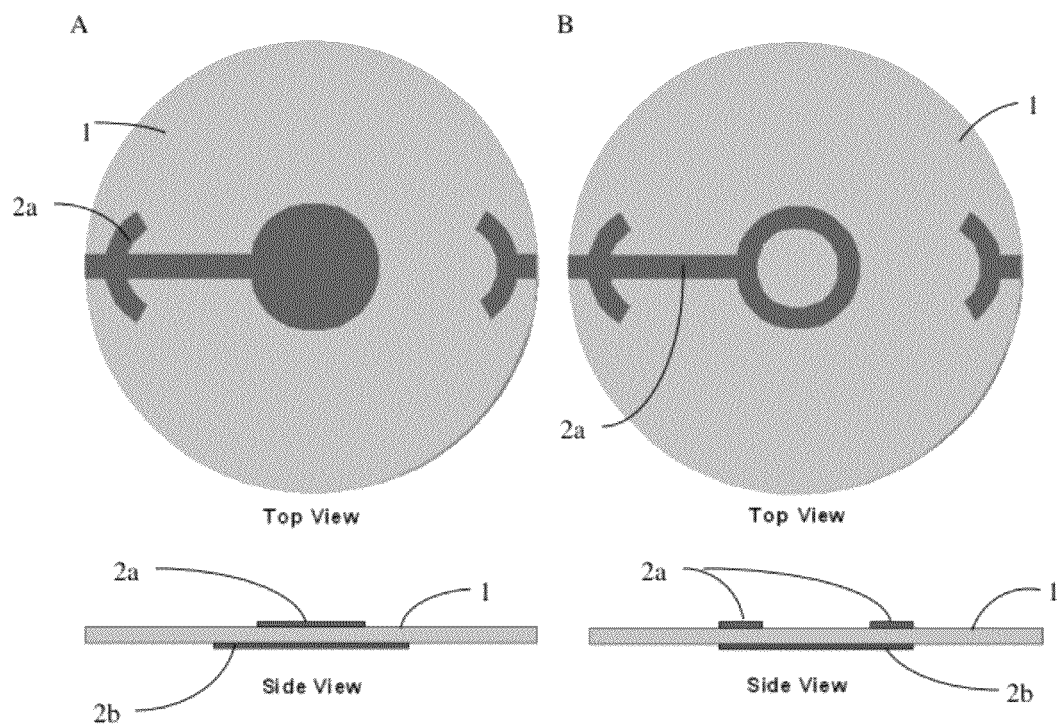
FIGS. 1(a) and (b) are illustrations of simple electrode designs for a TSM quartz resonator: (a) solid 'n-m' electrode configuration, and (b) single ring electrode configuration.

TSM devices described herein consist of an upper electrode $2a$ and a bottom electrode $2b$ mounted onto a piezoelectric crystal material 1, such as those seen in FIGS. 1(a) and (b). Development of analytical mathematical models for predicting the mass sensitivity of TSM devices having simple electrode configurations has continued since Sauerbrey's initial study of the frequency shift due to mechanical loading on the device surface (G. Sauerbrey. Z. Phys., vol. 155, pp. 206-222, 1959). Typically, these models are generated through either a resonant frequency analysis or three-dimensional perturbation modeling of the wave motion in the quartz substrate. However, these techniques share a common assumption that the mass sensitivity is proportional to the square of the quartz particle displacement amplitude (F. Josse, et al., "Analysis of the radial dependence of mass sensitivity for modified-electrode quartz resonators." *Analytical Chemistry*, vol. 70, pp. 237-247, 1998; F. Lu, et al., "Quartz crystal microbalance with rigid mass partially attached on electrode surfaces." *Sens. Actuators A: Phys.*, vol. 112, pp. 203-210, 2004; Z. Wang, et al., "Perturbation method for analyzing mass sensitivity of planar multilayer acoustic sensors." *IEEE Trans. Ultrason., Ferroelect., Freq. Contr.*, vol. 43, pp. 844-851, 1996; S. W. Wenzel and R. M. White, "Analytic comparison of the sensitivities of bulk-wave, surface-wave, and flexural plate-wave ultrasonic sensors." *Appl. Phys. Lett.*, vol. 54, pp. 1976-1978, 1989).

Figure 2:
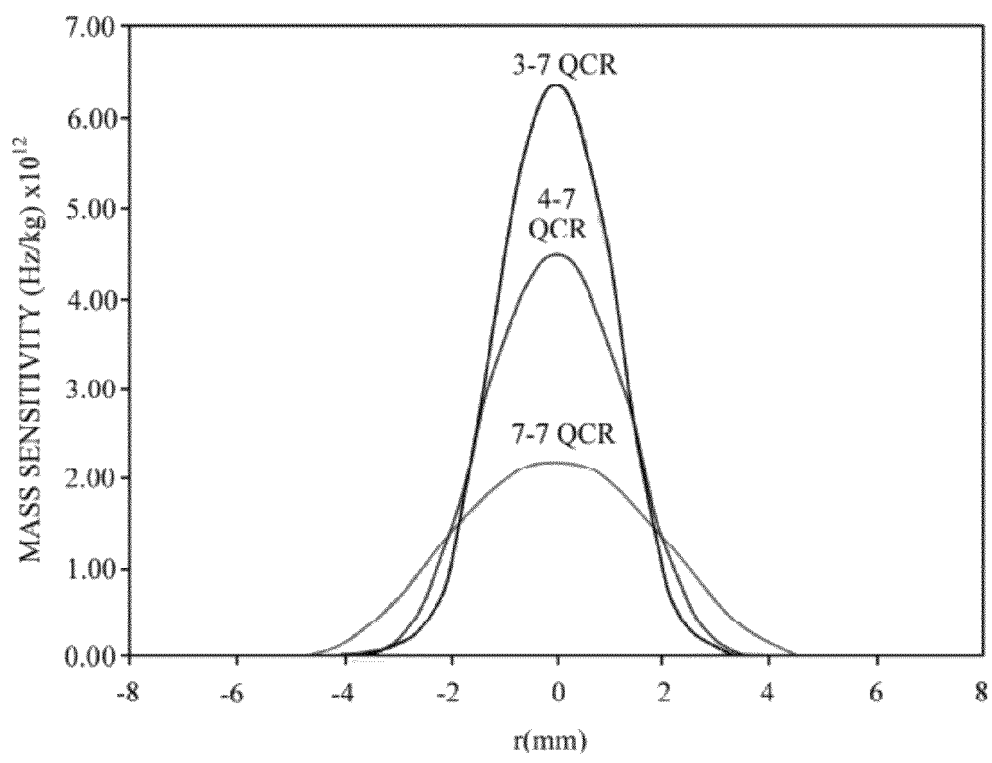
FIG. 2 is a graph of the modeled mass sensitivity of thickness shear mode resonators having differing 'n-m' electrode thicknesses.

Modifications of the surface of the resonator are necessary to confine the analyte sample being measured within the region of constant mass sensitivity, including ensuring the droplet remains stationary and considered as a point mass, seen in FIG. 2. Presented below are the theoretical and experimentally measured mass sensitivity distributions for a ring electrode configuration having inner and outer diameters of 4 and 10 mm, respectively, and a model driven Cr/Au electrode thickness predicted to produce a uniform mass sensitivity. Additionally, descriptions of the fabrication of the TSM devices and a novel experimental apparatus constructed to measure mass sensitivity distribution are presented.

Example 1

TSM Device Design

The device eliminates the non-uniformity in mass sensitivity of commercially available devices through modification of the electrode design. The models relate frequency shift to mass accumulated on surface of TSM device through Sauerbrey's equation:

$$m_f = \frac{\Delta f \rho_q v_q}{2 f_r^2} \quad (1)$$

Figure 3:
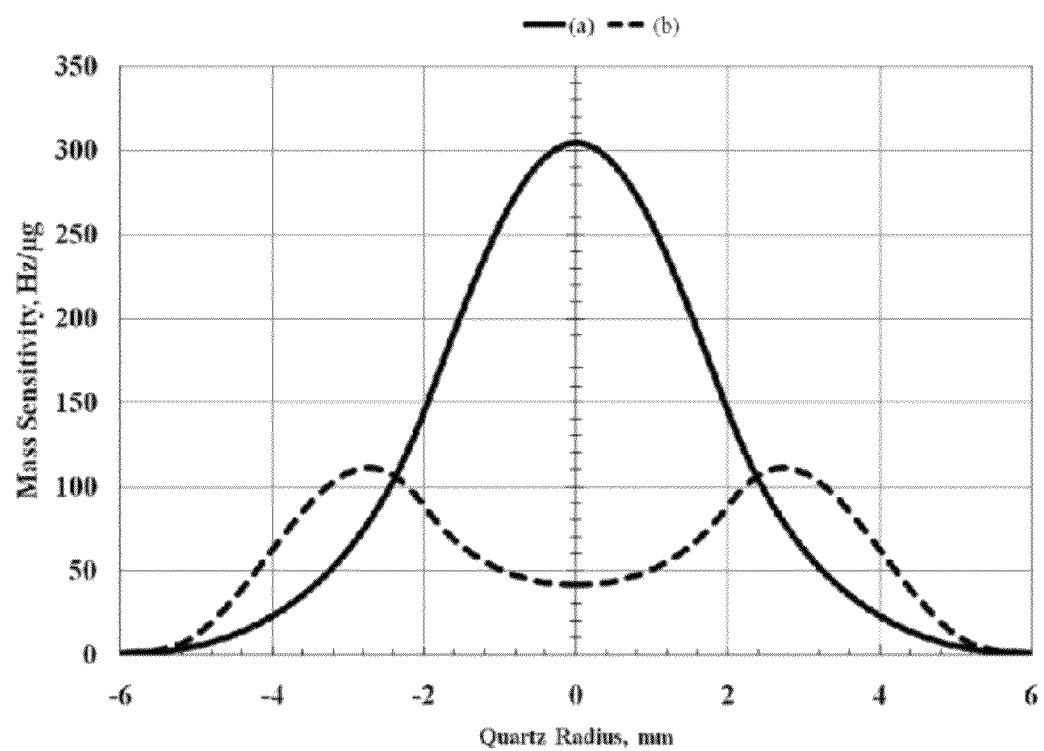
FIG. 3 is a graph showing the theoretical mass sensitivity distributions for simple electroded 5 MHz TSM devices: (a) 'n-m' electrode configuration with top and bottom diameters of 4 and 10 mm, respectively, with R=0.0036 and (b) ring electrode configuration with inner and outer diameters of 4 and 10 mm, respectively, with R=0.0334.
Figure 4:
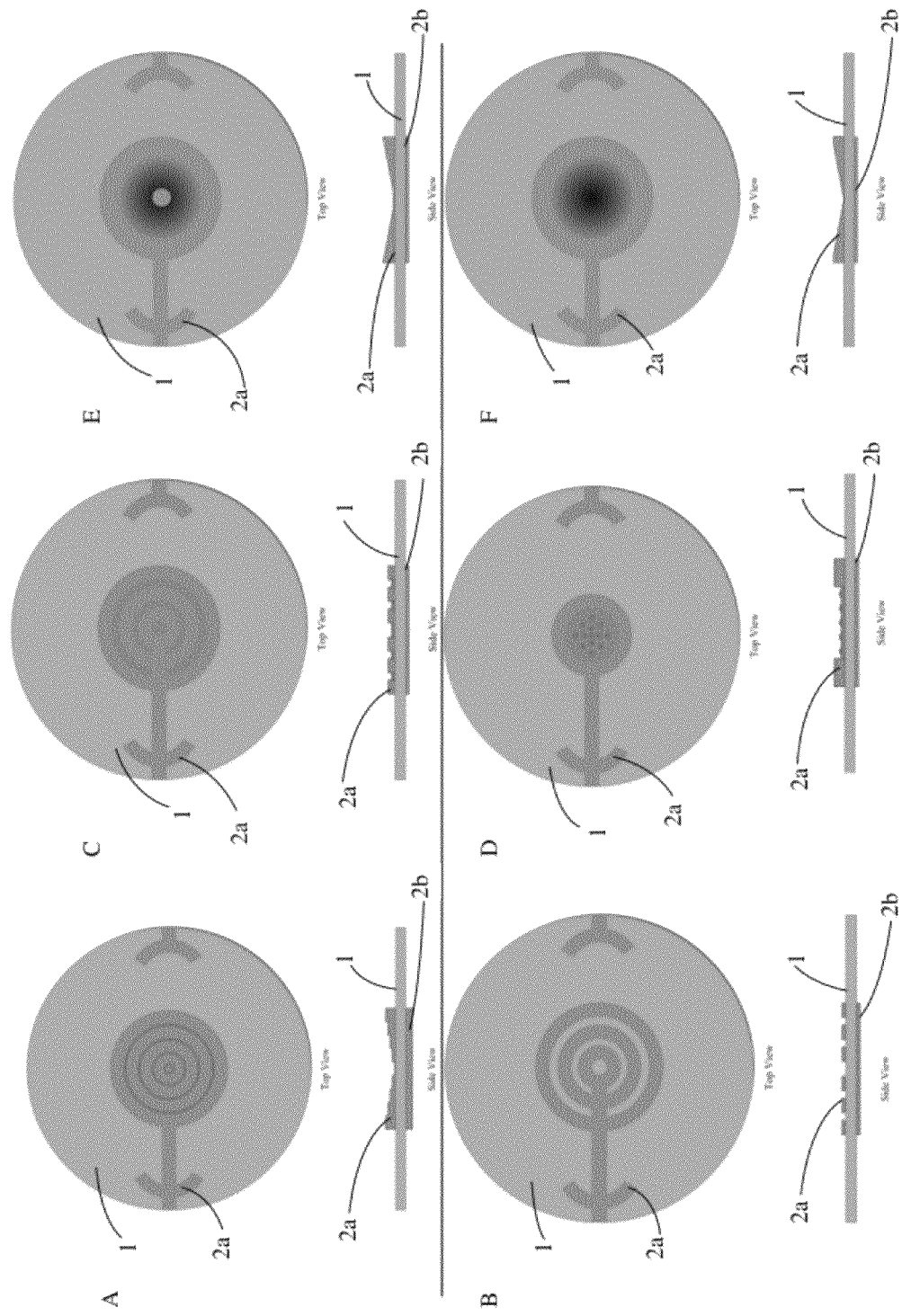
FIGS. 4(a)-(f) are illustrations of the plate and electrode configurations for the device. The left column displays the top view and side view of the quartz plate with the electrode configuration. The electrode configurations are: (A) a tiered ring electrode; (B) concentric ring electrode; (C) a concentric ring electrode with a conductive material between the electrodes; (D) a single ring electrode with shorted metal dots within the ring; (E) a wedge-shaped electrode; and (F) a conical etched electrode. Note that the bottom electrode has the outer dimensions of the top electrode and is set to be solid.

A model was employed herein, based upon a resonance analysis across the sensor platform, which is capable of producing displacement amplitude distributions for both the simple "n-m" and ring electrode cases (F. Josse, et al., "Analysis of the radial dependence of mass sensitivity for modified-electrode quartz resonators." *Analytical Chemistry*, vol. 70, pp. 237-247, 1998). The radial mass sensitivity profile of a TSM device is influenced by the electrode configuration. Utilizing the analytical model of Josse, et al. (F. Josse, et al., "Analysis of the radial dependence of mass sensitivity for modified-electrode quartz resonators." *Analytical Chemistry*, vol. 70, pp. 237-247, 1998) for both the simple 'n-m' and ring electrode cases, it was determined that the ring configuration is capable of producing a uniform mass sensitivity distribution due to the bimodal response in mass sensitivity across the sensor platform. FIG. 3 shows the bimodal response of mass sensitivity for the ring electrode, in comparison to that of the n-m design. Analyzing possible electrode designs, shown in FIG. 4, it was determined that the ring configuration is capable of producing a uniform mass sensitivity distribution due to the bimodal response in mass sensitivity across the sensor platform. Given this, only the model calculations for the mass sensitivity distributions of the ring electrode designs were considered.

Mechanical mass sensitivity for any TSM device, as a function of the quartz radius, is governed by the particle displacement amplitude resulting from the shear horizontal wave propagating through the quartz substrate.

$$S_f(r) = \frac{|u_1(r)|^2}{2\pi \int_0^\infty r|u_1(r)|^2 \, dr} C_f \quad (2)$$

where, $$C_f = \frac{2f_r^2}{\rho_q v_q} \quad (3)$$

Determination of the particle displacement amplitude, $|u_1(r)|$, is dependent upon the electrode geometry, as well as the electrode mass loading factor, R, the ratio of the overall electrode areal mass, $\rho_e h_e$, to that of the quartz substrate, $\rho_q h_q$, expressed as:

$$R = \frac{\rho_e h_e}{\rho_q h_q} \quad (4)$$

The electrode mass loading factor is an important parameter setting both the magnitude of the mass sensitivity and the extent to which the profile tapers toward the center of the quartz surface for the ring electrode case. The particle displacement amplitudes for ring electrodes from the model in (F. Josse, et al., "Analysis of the radial dependence of mass sensitivity for modified-electrode quartz resonators." *Analytical Chemistry*, vol. 70, pp. 237-247, 1998) are given by the following equation:

$$u_1(r) = \begin{cases} AI_0(k_r^p r) & 0 \leq r \leq a \\ BJ_0(k_r^e r) + CN_0(k_r^e r) & a \leq r \leq b \\ DK_0(k_r^u r) & b \leq r \leq \infty \end{cases} \quad (3)$$

The radial boundary variables a and b represent the inner and outer radii of the ring electrode, respectively. For the ring electrode case, the signal electrode is the ring structure and the ground is a solid electrode with a radius equal to the outer radius of the ring, b. $I_0$, $J_0$, $N_0$, and $K_0$ are Bessel functions of the zeroth kind. The amplitude constants A, B, C, and D are obtained by solving a set of linear homogeneous equations, as described in (F. Josse, et al., "Analysis of the radial dependence of mass sensitivity for modified-electrode quartz resonators." *Analytical Chemistry*, vol. 70, pp. 237-247, 1998).

$$\begin{bmatrix} I_0(k_r^p a) & -J_0(k_r^e a) & -N_0(k_r^e a) & 0 \\ -k_r^p I_1(k_r^p a) & k_r^e J_1(k_r^e a) & k_r^e N_1(k_r^e a) & 0 \\ 0 & J_0(k_r^e b) & N_0(k_r^e b) & -K_0(k_r^u a) \\ 0 & -k_r^e J_1(k_r^e b) & -k_r^e N_1(k_r^e b) & k_r^u K_1(k_r^u b) \end{bmatrix} \cdot \begin{bmatrix} A \\ B \\ C \\ D \end{bmatrix} = 0 \quad (5)$$

Therefore, changing the electrode configurations from 'n-m' to ring broadens the mass sensitivity distribution and yields peaks at both of the outer boundaries of the ring electrode. The distribution of a ring electrode exhibits promise to produce uniform mass sensitivity, seen in FIG. 3.

Figure 5:
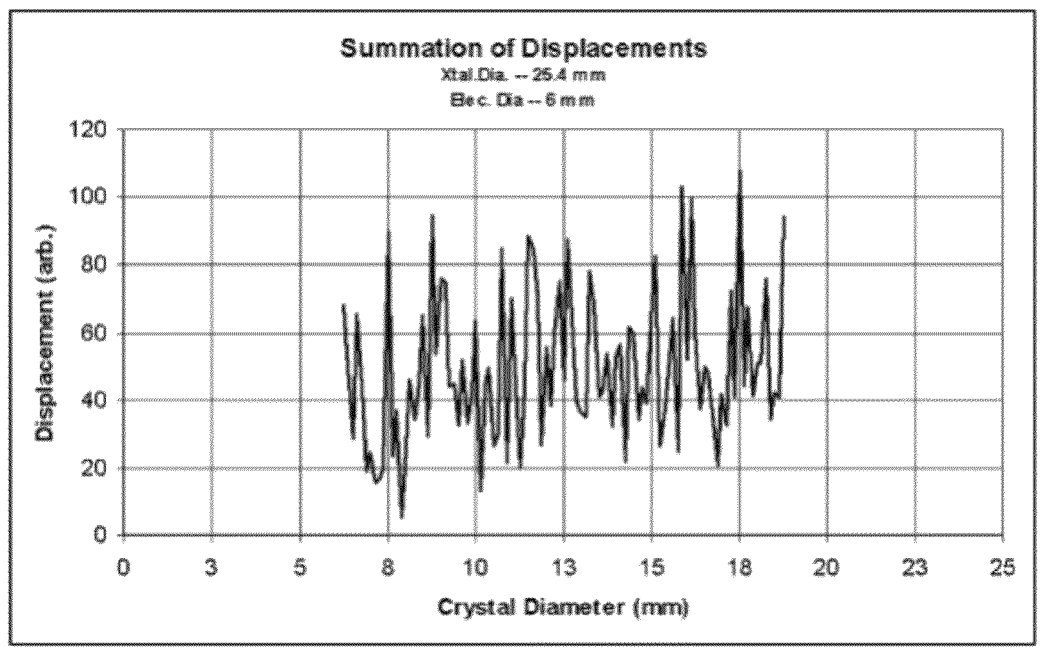
FIG. 5 is a graph of the finite element modeling (FEM) simulation of a 5 MHz TSM resonator using harmonic quartz.

A finite element modeling (FEM) simulation of a 5 MHz TSM resonator was developed by modeling a mass sensitivity device with a harmonic quartz, using refined or course mesh and differing electrodes, seen in Table 1 and FIG. 5.

TABLE 1

Results of Model

| Type | Piezoelectric Substrate | Adhesion Layer | Electrode |
|---|---|---|---|
| Type | Quartz | Chromium | Gold |
| density/(kg/m³) | 2,649 | 7,150 | 19,300 |
| Thickness/m | $3.2 \times 10^{-4}$ | $1.0 \times 10^{-8}$ | $2.0 \times 10^{-7}$ |

Using the finite element modeling (FEM) simulation at 5 MHz, the displacement amplitudes are confined to the electroded region. The displacement symmetry is almost apparent on either side of resonator center.

Example 2

TSM Device Fabrication and Electrical Characterization

Figure 6:
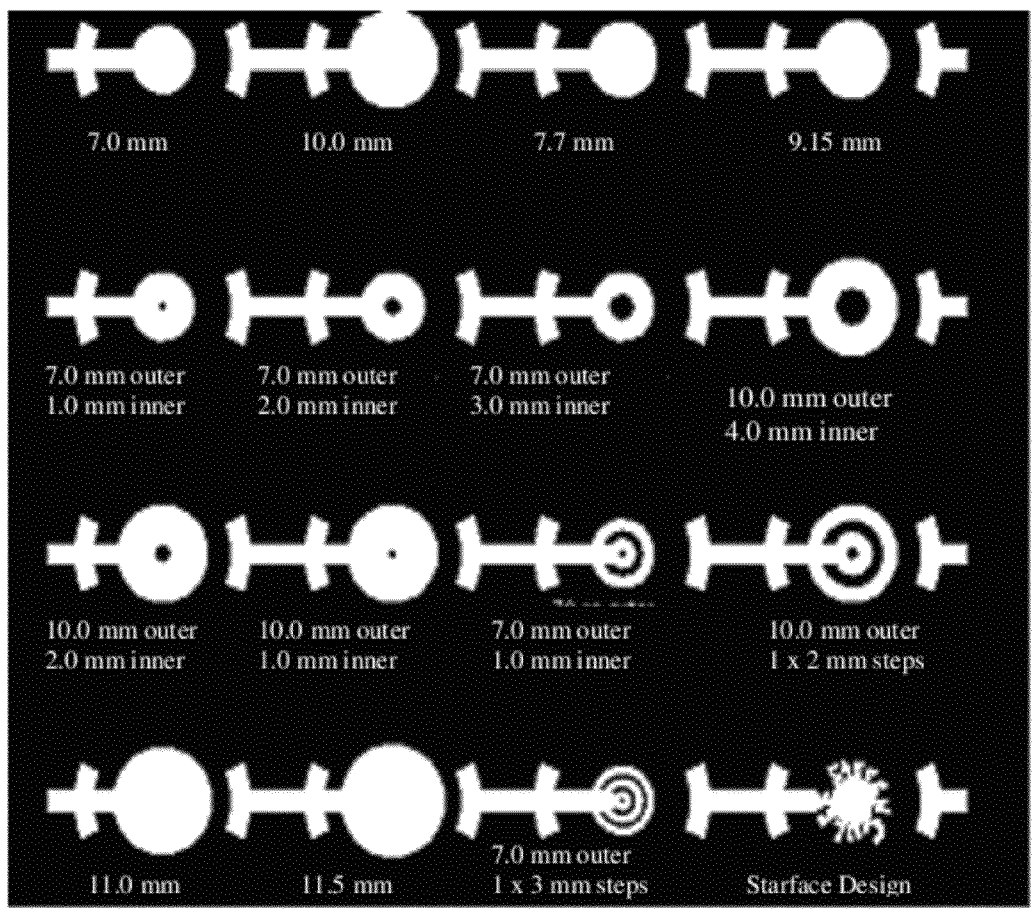
FIG. 6 is a set of photomask images used in preparing the different electrodes for thickness shear mode resonator devices.
Figure 7:
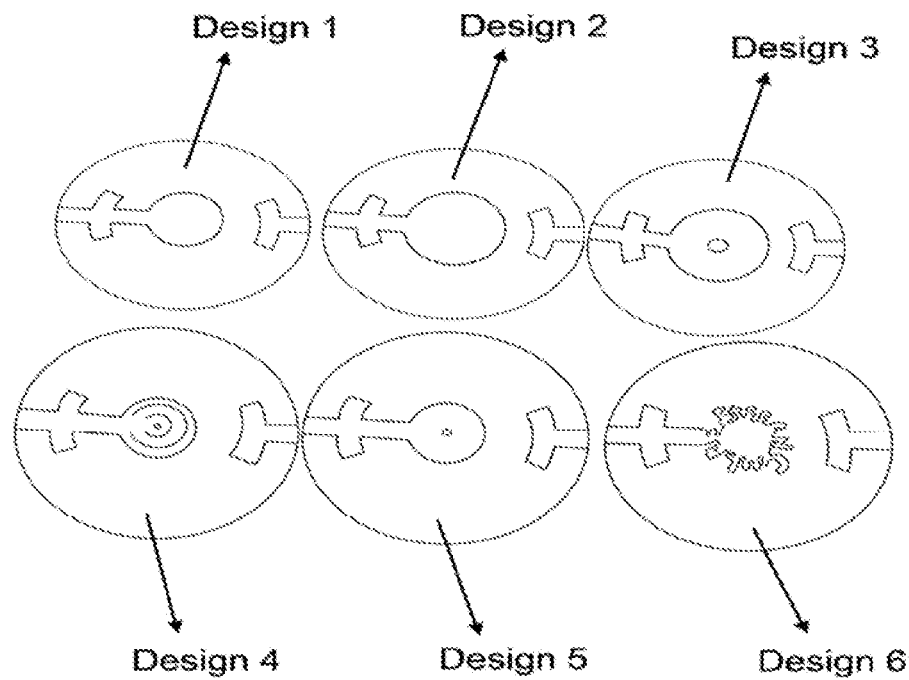

To produce the TSM devices, a photolithographic process and metal deposition were conducted. The blank quartz substrates utilized were polished 1-inch diameter AT-cut crystals with an operating frequency of 5 MHz (Tangidyne Corp.). These quartz blanks were cut by the manufacturer at an angle of 35° with a one-minute precision and polished with 0.01 μm grit. A 2.0 ml droplet of photoresist (Futurrex, Inc., NR9-1500PY) was deposited at the center of the blank and spun-off at 3500 rpm for 30 seconds in a spin-coater (Laurell Tech.). The resulting thickness of the resist layer was not characterized. Once the photoresist was soft-baked in an oven at 90° C. for 15 minutes, it was exposed to viable electrode designs on a high-resolution chromium/glass photomask (Advanced Reproductions Corp.), as seen in FIG. 6, using a long-wave (365 nm) UV lamp for 45 seconds (Blak-Ray, model B-100W). After exposure, the resist-coated crystal was baked again in the oven at 120° C. for another 15 minutes, and developed in developer solution followed by a rinsing in deionized water. The chromium adhesion and gold layers were deposited to the desired thicknesses in a thermal evaporator, approximately 75±10 Å and 1050±10 Å, respectively. Lift-off of the photoresist was done in acetone and facilitated in a sonic water bath. The fabrication process was repeated for both sides of the crystal. Six TSM devices were created, seen in FIG. 7 and Table 2. Good adhesion of the metallic electrode layers to the quartz surface was observed.

TABLE 2

Characterization of TSM fabrication.

|  | Top | | Bottom | |
| --- | --- | --- | --- | --- |
|  | Au | Cr | Au | Cr |
| Pressure (Torr) | 0.00002 | 0.00002 | 0.00002 | 0.00002 |
| Rate (Å/s) | 0.6 | 0.1 | 10 | 10 |
| Thickness (Å) | 1000 | 100 | 1000 | 100 |

Figure 8:
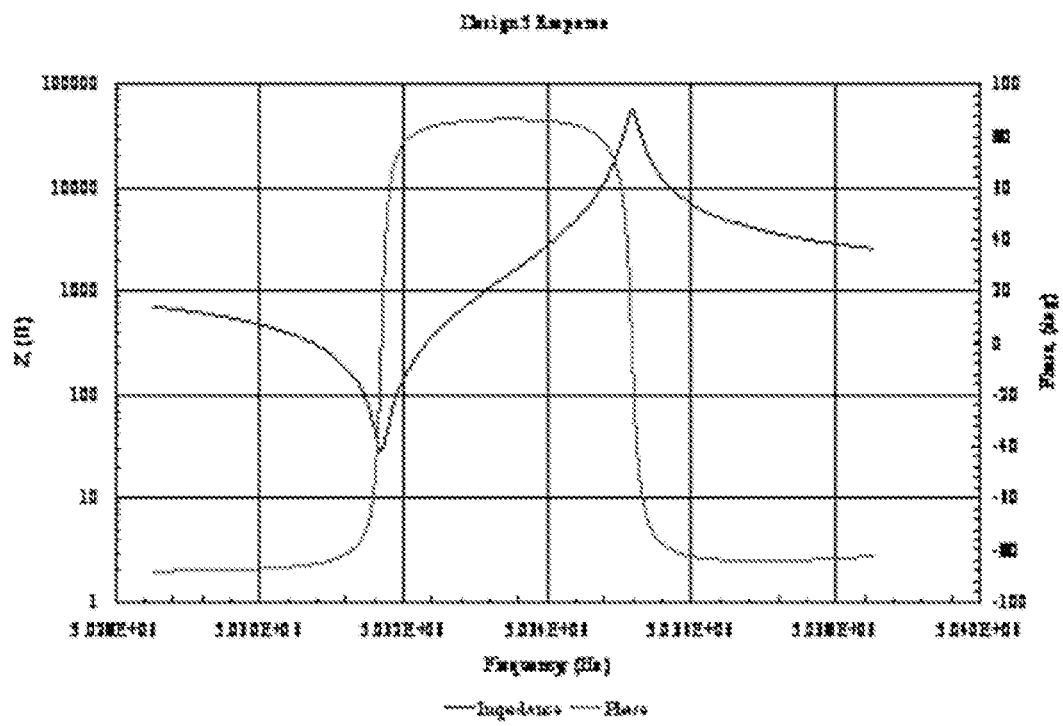
FIG. 8 is a graph of the impedance and phase response of the Design 5, measured using an Agilent 4294A impedance analyzer.
Figure 9:
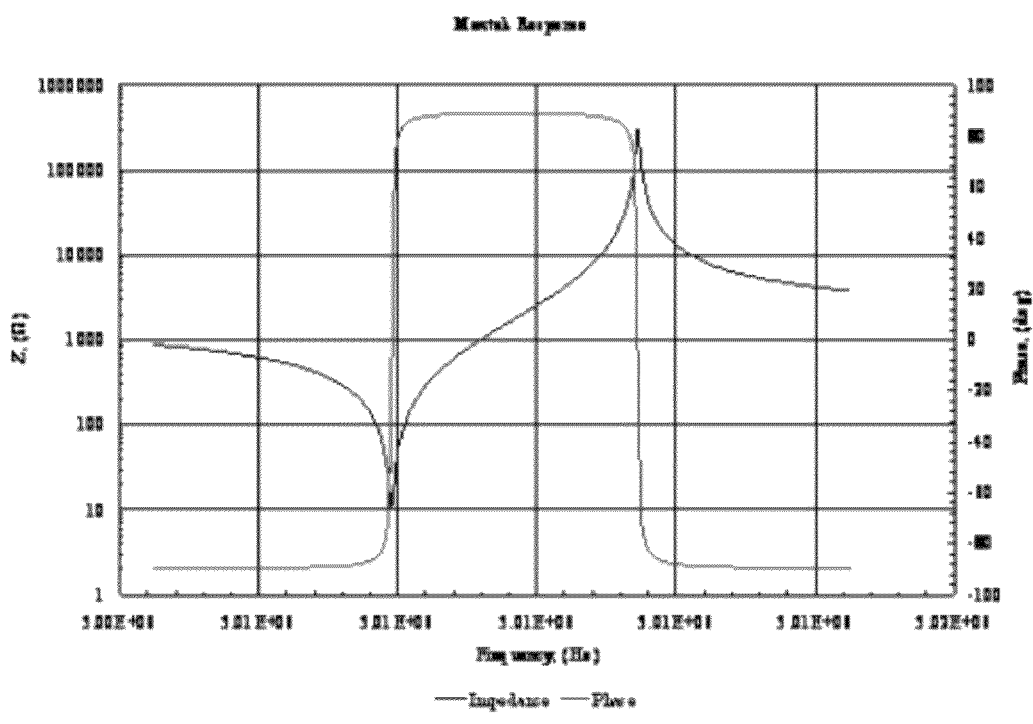
FIG. 9 is a graph of the impedance and phase response of the Maxtek design, measured using an Agilent 4294A impedance analyzer.

The fabricated devices were characterized for further analysis. Impedance and phase response measured using an Agilent 4294A impedance analyzer, seen in FIGS. 8 and 9. Equivalent circuit parameters were then obtained by modeling the TSM resonator as a BVD equivalent circuit, seen in Table 3. It is noted that differences in resistances result from the design complexity and the silver conductive polymer used for the wrap-around electrode.

TABLE 3

Parameter characterization of TSM resonator designs.

| Design # | fs/MHz | fp/MHz | R/Ω | L/mH | $C_1$/fF | $C_0$/pF |
| --- | --- | --- | --- | --- | --- | --- |
| 1 | 5.0327 | 5.0308 | 56.4 | 27.6 | 36.2 | 22.7 |
| 2 | 5.0276 | 5.0246 | 44.9 | 17 | 58.9 | 26.8 |
| 3 | 5.0255 | 5.0235 | 40.3 | 27.5 | 36.5 | 23.2 |
| 4 | 5.0383 | 5.0367 | 71.4 | 41.1 | 24.3 | 19.6 |
| 5 | 5.0335 | 5.0317 | 27 | 33.2 | 30.1 | 21.8 |
| 6 | 5.0359 | 5.034 | 135.3 | 33.2 | 30.1 | 21.8 |
| Maxtek | 5.0115 | 5.0079 | 9.4 | 41.3 | 24.4 | 17.3 |

Utilizing computations based upon the analytical modeling, discussed in Example 1, indicate that mass loading factors R exist which can produce uniform mass sensitivity distributions for many ring electrode configurations. Ring electrode TSM devices having different R-values were fabricated and tested.

Example 3

Mass Sensitivity Distributions

Various techniques to measure the mass sensitivity across the surface plane of a TSM resonator have been developed including x-ray diffraction to characterize quartz particle vibration, surface charge distribution measurement, and characterization of optical speckle patterning produced by coherent light incident across the quartz surface. However, all of these methods have significant limitations, discussed in (P. J. Cumpson and M. P. Seah, "The quartz crystal microbalance; radial/polar dependence of mass sensitivity both on and off the electrodes." *Meas. Sci. Tech.*, vol. 1, pp. 544-555, 1990; P. J. Cumpson, "Quartz crystal microbalance: A new design eliminates sensitivity outside the electrodes, often wrongly attributed to the electric fringing field." *J. Vac. Sci. Tech. A*, vol. 15, pp. 2407-2412, 1997; V. M. Mecea, "A new method of measuring the mass sensitive areas of quartz crystal resonators." *J. Phys. E: Sci. Instr.*, vol 22, pp. 59-61, 1989).

Another approach is an ink dot method where dots from a fine-tipped felt pen are placed at precise radial positions and the resulting frequency shifts are recorded. This technique is effective and efficient provided that the mass of each dot deposited is reproducible, which is very difficult to achieve. Thus, a novel apparatus was developed using a similar technique; but eliminating the issue of reproducible mass upon each deposit. The modified TSM resonators were placed in a stainless steel test cell with drilled channels allowing heated water circulation for maintaining temperature, set at 60° C., and facilitating droplet evaporation. The frequency of the bare crystal at the system temperature was monitored using a high-precision frequency counter (±0.01 Hz) and simple oscillating circuit (SRS, model QCM-200), and allowed to stabilize. Droplets having a known mass and containing a specific concentration of dissolved polymer or 0.65 wt % hydroxypropylcellulose (HPC)/water solution, were deposited at precise radial positions using the microvalve within the area of constant mass sensitivity of the TSM device. Because microliter-sized droplets dispensed from the syringe are too large for the modified TSM devices due to wetting effects prompting spreading of the droplets outside the sensing area of the device, mass sensitivity measurements were made by depositing minute droplets using a microvalve (TechElan, model SMLD-5b, <5% CV in dispensing) at radial positions extending from the resonator center.

The precise positioning of the droplets along a radial axis was achieved using both a Newmark Systems linear (model NLE-50, 0.01 µm resolution) and rotary (model RT-2, 0.32 arc-seconds resolution) micro-positioner. After deposition of a droplet, the frequency of the resonator was allowed to stabilize to ensure complete evaporation and the resulting shift determined. Based on the known mass deposited and the frequency shift, the mass sensitivity at a radial position is quantified. Measurements were taken along radial axes extending from 0=0° to 180° with a step-interval of 30° to account for any anisotropic effects due to the quartz substrate.

Figure 10:
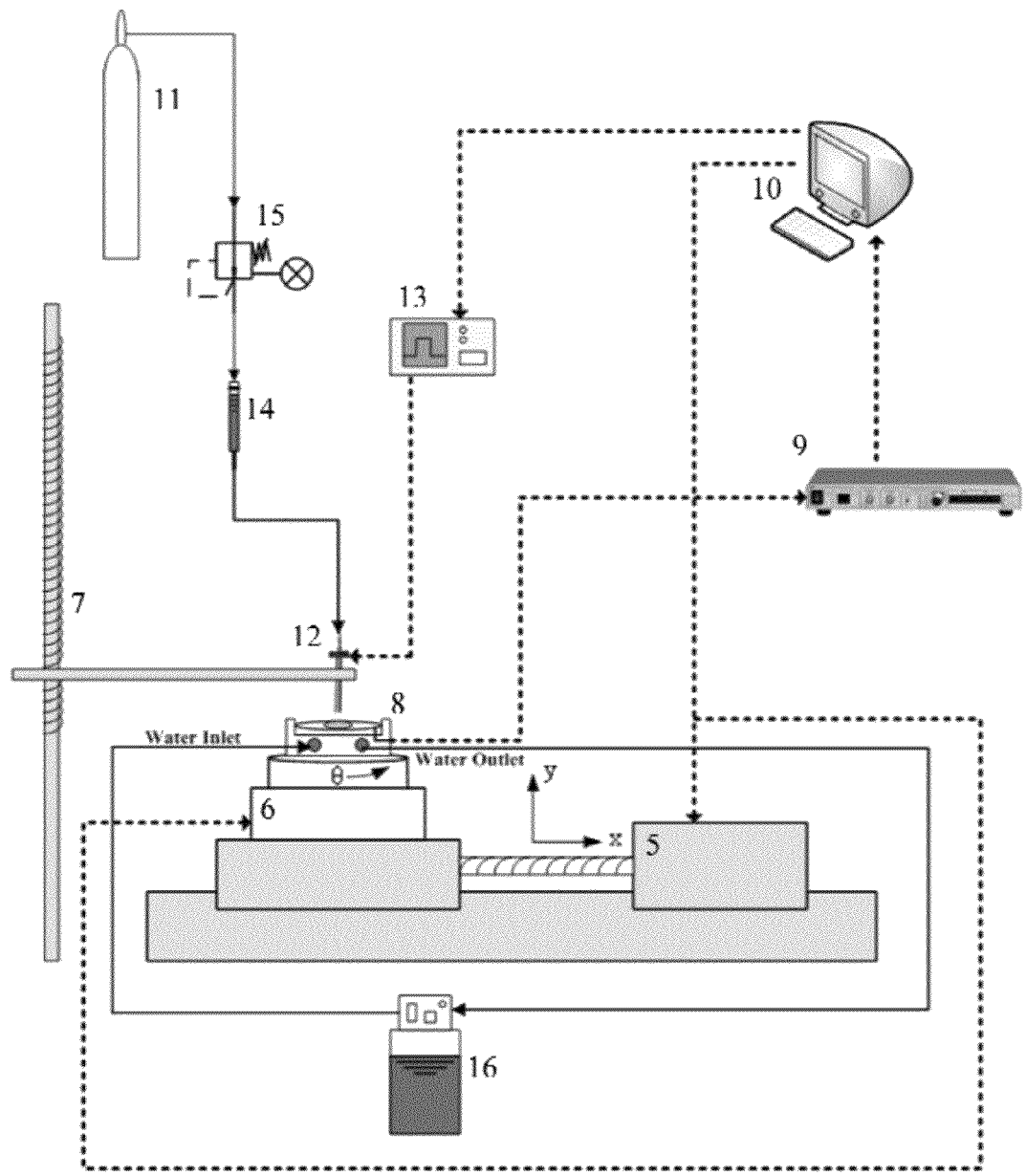
FIG. 10 is detailed schematic of the experimental apparatus for measurement of the mass sensitivity distributions of TSM devices.

The mass of each droplet was determined to be 170.1±8.4 µg by dispensing 150 droplets in a weighing tray full of oil and weighed using a mechanical mass balance (Denver Instrument Company, model 250-A, 0.01 mg tolerance). The 5% discrepancy in the droplet mass can be attributed to both the potential evaporation of methanol before it reaches the oil and the tolerance of the balance. FIG. 10 provide schematics of the experimental apparatus, with Newmark systems linear micropositioner 5, Newmark systems rotary micropositioner 6, and manual vertical micropositioner 7 being used to position a TSM device inside TSM resonator stainless-steel test cell 8. Test solution is added using TechElan microvalve with driver 12, controlled by gas driven syringe 14, Marsh Bellofram low pressure regulator 15, and using nitrogen cylinder 11. Test solution may be dried using Thermo Neslab RTE 740 heater/chiller water circulator 16. The position and test systems of the device and recording are performed using computer workstation 10. Results are then collected using Stanford Research Systems QCM-200 Frequency Counter and Oscillator Circuit 9, and Agilent Pulse Generator 13. Additionally, details of the experiment including droplet characteristics and position interval are given in Table 4.

TABLE 4

Mass sensitivity experimental details.

| Parameter | Value |
| --- | --- |
| Droplets per position | 2 |
| HPC mass deposited per position, ng | 227 ± 20 |
| Position step interval, mm | 0.5 |

Figure 11:
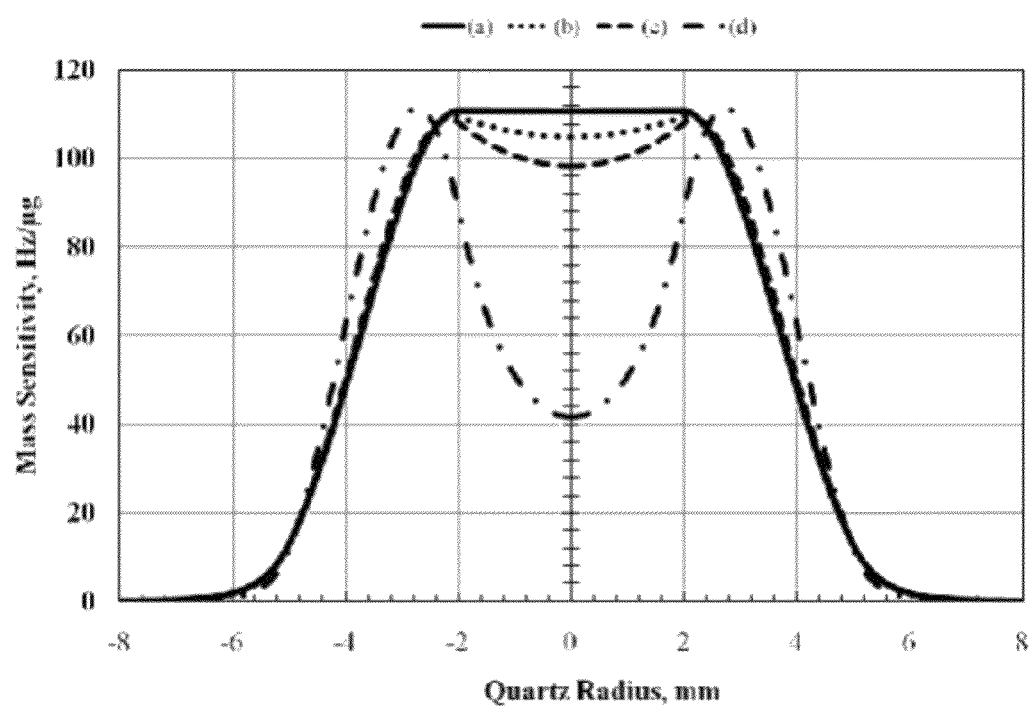
FIG. 11 is a graph of the mass sensitivity distributions for a ring electrode 5 MHz TSM device having inner and outer diameters of 4 and 10 mm, respectively, with: (a) R=0.0025, (b) R=0.0033, (c) R=0.0042, and (d) R=0.0088.

FIG. 11 shows how the mass sensitivity distribution for a ring electrode TSM device having inner and outer diameters of 4 and 10 mm, respectively, changes when R is varied from 0.0025 to 0.0088. For R equal to 0.0025, corresponding to Cr/Au thicknesses of 75 Å and 1050 Å, respectively, the mass sensitivity profile becomes uniform within the active sensing area. Although these ring design parameters do indeed produce a uniform sensitivity distribution, it should be noted that the maximum sensitivity is less, such as one order of magnitude, than commercially available 5 MHz 'n-m' electrode TSM devices. The reduced mass sensitivity of the ring electrode design results from the confinement of both the excited acoustic wave and the energy associated with the driving wave within the fully electroded region, between the ring radii a and b (F. Josse, et al., "Analysis of the radial dependence of mass sensitivity for modified-electrode quartz resonators." *Analytical Chemistry*, vol. 70, pp. 237-247, 1998). All the same, the mass sensitivity of the proposed ring design is sufficient for most nanogram mass detection applications. Extension of the design optimization to higher frequency devices, such as 11 MHz AT-cut quartz crystals, would improve the overall mass sensitivity of a ring electrode device; however, vibration instability due to increased energy trapping would be greater for higher frequency devices (F. Josse, et al., "Analysis of the radial dependence of mass sensitivity for modified-electrode quartz resonators." *Analytical Chemistry*, vol. 70, pp. 237-247, 1998).

Figure 12:
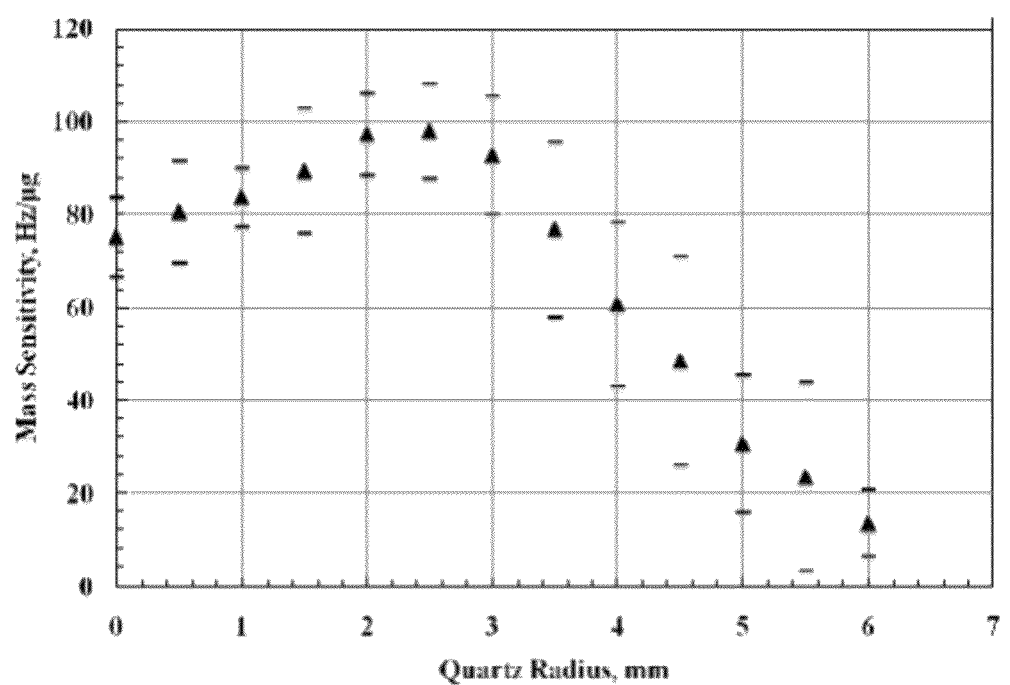
FIG. 12 is a graph of the experimental mass sensitivity distribution for a ring electrode 5 MHz TSM device having inner and outer diameters of 4 and 10 mm, respectively, with R=0.0025.

FIG. 12 presents the experimental mass sensitivity measurements. The experimental results represent multiple measurements taken over different radial alignments extending from θ=0° to 180° with a step-interval of 30°. Results agree well with theory; however, there still exists a remnant bimodal response in the distribution. Uncertainty in the electrode thicknesses, approximately ±10 Å, explains the discrepancy given that the mass sensitivity profile is sensitively dependent on the electrode mass loading. Additionally, variable scatter in the measured data, denoted in the error bars expressing one standard deviation, was observed. Anisotropy of the quartz is likely a contributor to the approximately 10-15% standard deviation (error bars) reported in FIG. 12, where data are averaged over all radial directions. This situation improves when mass sensitivity is measured along a single radial direction, in which case the standard deviation is 3%. However, it is difficult to design a practical nanobalance wherein mass is deposited along a single radial direction. Hence, data averaged over all radial directions have been presented. The inherent vibration instability of the ring electrode configuration due to energy trapping resulting from the coupling of the oscillating modes within the electroded region, between the radii a and b, (F. Josse, et al., "Analysis of the radial dependence of mass sensitivity for modified-electrode quartz resonators." *Analytical Chemistry*, vol. 70, pp. 237-247, 1998; E. Ansorge, et al., "Plano-convex shaped langasite microbalances for high temperature applications." Proceedings, IEEE Sensors 2007, Atlanta, Ga., USA, 2007) also contributes to the scatter.

Example 4

Droplet Gravimetry Measurements

Figure 13:
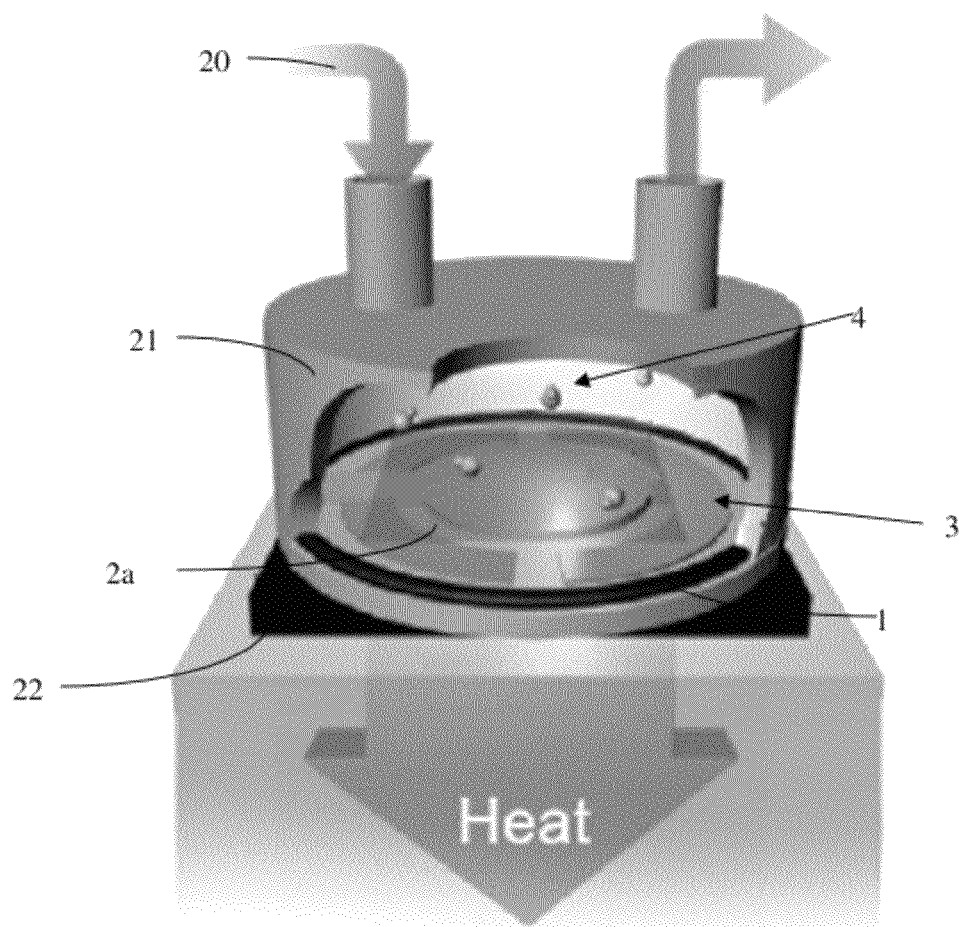
FIG. 13 is an illustration of the mass/heat flow sensor and sample chamber of the Masscal™ G1 calorimeter.

The primary motivation for developing a TSM device exhibiting uniform mass sensitivity and high frequency stability is to incorporate the device into a commercially available nanobalance/calorimeter and provide a viable and inexpensive gravimetric technique for determining NVR levels in high purity solvents. The Masscal™ G1 quartz crystal microbalance/heat conduction calorimeter (www.masscal.com) was utilized with the fabricated and modified TSM devices to measure the NVR in solvent solutions by droplet gravimetry. The G1 consists of a thermopile/aluminum heat sink and a simple oscillator circuit with frequency counter for simultaneous measurement of thermal power and resonator frequency shift. Monitoring of heat flow and frequency shift allows for determining droplet volume (utilizing the latent heat of vaporization) and NVR residue mass accumulation on the TSM device surface, respectively. FIG. 13 provides a detailed schematic of the G1 instrument, showing the TSM sensor 3, comprising piezoelectric crystal material 1, upper electrode 2a and a bottom electrode 2b. TSM sensor 3, is mounted in isothermal microcalimeter chamber 21, and thermally connected to thermopile 22. Test solution is added, forming sample film coating 4, which may be dried or moistened with humidity controller 20.

Droplet gravimetry is conducted in the G1 by depositing microliter size droplets of histological grade methanol (Fisher Scientific), using a graduated syringe onto the resonator surface in the sample chamber and monitoring the thermal power flow and frequency shift until the system stabilizes. The results from these measurements exhibited unreasonable standard deviations in the NVR. Incorporation of a microvalve, as discussed in Example 3, into the G1 eliminated this shortcoming and allowed accurate measurement of NVR by droplet gravimetry. It is essential that the system stabilize to ensure that the droplet has evaporated to dryness. NVR levels in solvents are determined by droplet gravimetry from the following equations (A. Smith, "Gravimetric analysis of non-volatile residue from an evaporated droplet, using the quartz crystal microbalance/heat conduction calorimeter." *J. ASTM Intl.*, vol. 3, pp. 1-5, 2006).

Figure 14:
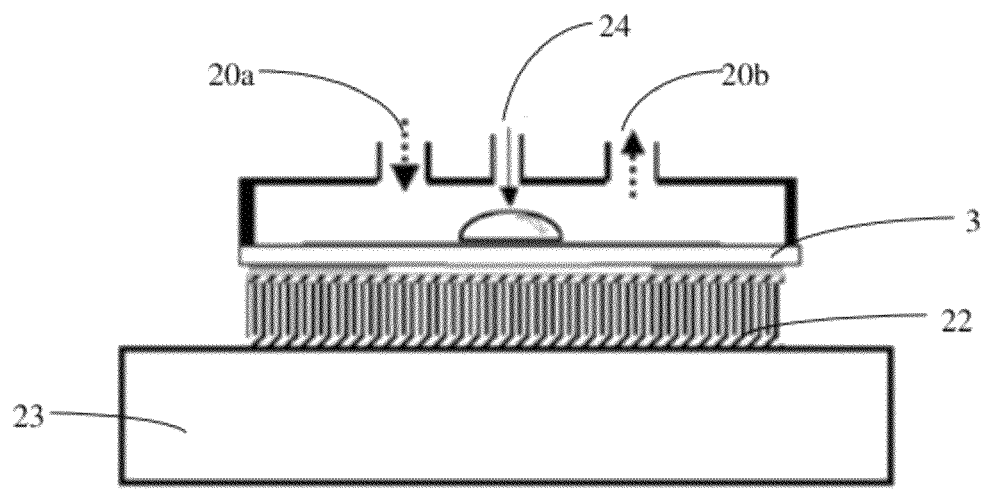
FIG. 14 is a schematic of the Masscal G1 Nanobalance/Calorimeter chamber used in NVR evaporation testing.

The gravimetric results of NVR levels in the methanol droplets are encouraging, given that they are within the range expected for the histological grade methanol utilized, even though the standard deviation in NVR is relatively high. NVR measurements of stock methanol solutions having a volume of 150 ml were conducted for comparison. These solutions were completely evaporated at 100° C. in a water bath and dried in a vacuum oven for one hour at 101° C. The residues were carefully weighed and, based on a methanol density of 0.7918 g/ml disclosed by the solvent manufacturer, the stock NVR level was determined to be within the range of 4.2 to 5.0 ppm. The devices were secured in Masscal G1 Nanobalance/calorimeter, shown in FIGS. 14, and 10 μL of high-purity methanol was injected into the chamber of the G1 apparatus. The apparatus uses TSM sensor 3, mounted onto thermopile 22, which is thermally connected to aluminum heat sink 23. Test solution 24 is added onto TSM sensor 3. Test solution 24 is dried onto the TSM sensor 3 using humidity controller 20, by adding dry air 20a and removing humid air 20b. The solvent was slowly evaporated at 40° C. using a slow feed of nitrogen and the perturbed TSM resonator characterized by measuring the heat required to evaporate the methanol, resonance frequency, and equivalent circuit parameters. The film are mass density was calculated using $$\Delta f = -C_q \rho_f h_f = -C_q \frac{m_f}{A_f} \tag{6}$$

The thermal power was then calculated as follows:

$$Q = \int P(t)dt = \frac{\rho_s V_s \Delta H_s^{vap}}{M_s} \qquad (7)$$

Here Δf is the frequency shift associated with the residue deposited, m, and $A_r$ are the residue film mass and area, respectively, and $C_q$ is the sensitivity factor. For a 5 MHz TSM device, the sensitivity factor is taken to be 56.3 Hz*cm²/μg. Additionally, Q and P(t) are the integral heat required to evaporate the droplet and the measured thermal power, $\rho_s$ and $V_s$ are the solvent density and volume, $\Delta H_s^{vap}$ is the latent heat of vaporization of the solvent, and $M_s$ is the molar mass of the solvent.

Figure 15:
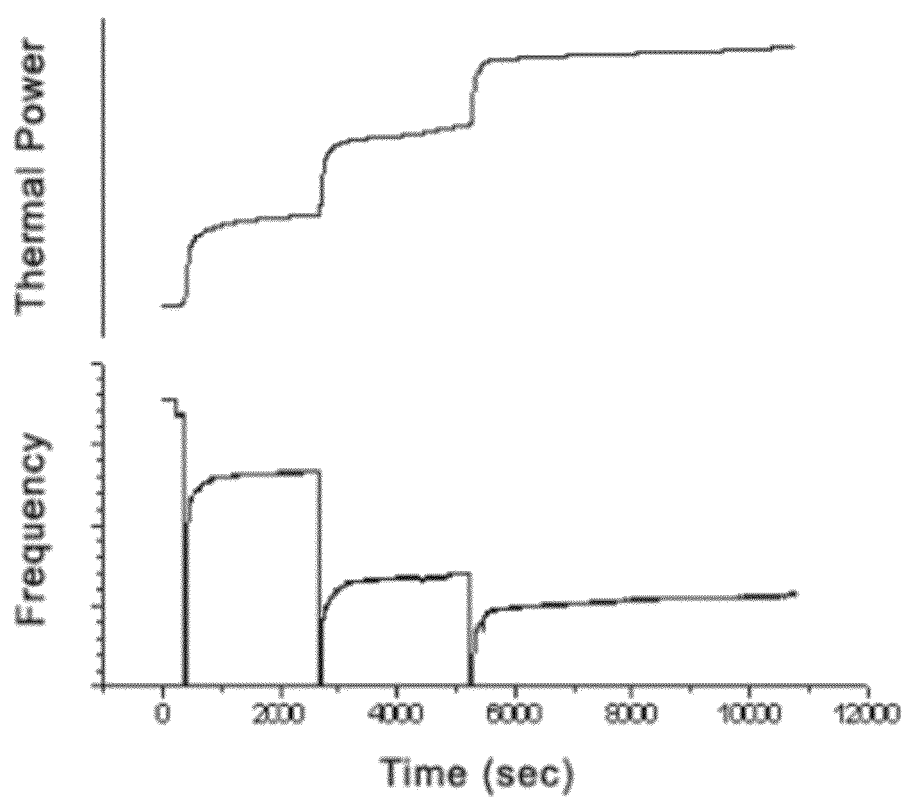
FIG. 15 is a graph of the frequency shift during testing in the Masscal G1 Nanobalance/Calorimeter chamber.

The results are summarized in Table 5. Mass sensitivity at each radial position, where mass deposition occurred, was extracted by comparing the corresponding frequency shift to the known polymer mass deposition. The heat needed to evaporate the test sample was in reasonable agreement with the volume dispensed, and the low surface tension of methanol prompted movement away from active center of resonator where mass sensitivity is constant. The frequency shift should be the same for a given volume dispensed, as seen in FIG. 15.

TABLE 5

TSM mass sensitivity characterization experimental results.

| Droplet # | 1 | 2 | 3 | Total |
|---|---|---|---|---|
| ΔF/Hz | −44 | −63 | −14 | −121 |
| Q = ∫P(t)dt/J | 9.22 | 8.86 | 7.97 | 26.06 |
| $m_r$/ng | 55 | 79 | 17 | 152 |
| $m_s$/mg | 8.07 | 7.75 | 6.98 | 22.8 |
| NVR/ppm | 6.8 | 10.2 | 2.5 | 6.5 ±3.9* |
| $\Delta V_{pred}$/μL | 10.2 | 9.8 | 8.8 | 28.8 |

*mean and standard deviation for 3 droplets

Therefore, to eliminate the radial variability of mass sensitivity that afflicts current TSM resonators, a surface treatment may be added to the TSM resonator that hinders the movement of an analyte droplet and creates a phobic/philic interface between the analyte and surface to ensure that the droplet is a point mass.

Droplet mass was determined from the integral heat associated with the droplet evaporation on the TSM device surface; with the incorporation of a microvalve for nanoliter dispensing in the Masscal G1 nanobalance/calorimeter. Methanol droplets were deposited using the microvalve. Given a residue film area of approximately 0.042 cm², determined by optical measurement of the residue radius, the residue mass and resulting NVR levels were calculated. The optical measurements of the film radius were made using a transmission microscope (Leica, model DMI-4000B, 5 μm resolution). Additionally, chemical modification of the gold surface with an alkanethiol self-assembled monolayer (SAM) would create a hydrophobic/hydrophilic surface for droplet containment. Detailed results are given in Table 6.

TABLE 6

Droplet Gravimetry

| Droplet | Δf, Hz | $m_r$, ng | NVR, ppm |
|---|---|---|---|
| 1 | −1.26 | 0.94 | 5.49 |
| 2 | −1.55 | 1.16 | 6.77 |
| 3 | −0.98 | 0.73 | 4.28 |
| 4 | −1.12 | 0.83 | 4.88 |
| 5 | −1.62 | 1.21 | 7.09 |
| total | −6.53 | 4.87 | 5.70 ± 1.2* |

*denotes average and standard deviation

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a shear mode quartz resonator, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A sensing device, comprising
a piezoelectric resonating material having a first face and a second face;
a first electrode disposed on the first face, wherein the first electrode has a ring geometry further comprising an inner ring diameter of 4 mm and an outer ring diameter of 10 mm;
a second electrode disposed on the second face, wherein the first electrode has a circular geometry further comprising an outer diameter of 10 mm;
a polymeric layer on at least a portion of the first electrode; and
wherein the sensing device has an electrode mass loading factor of 0.0025 to 0.0088, where $$R = \frac{\rho_e h_e}{\rho_q h_q}$$

where $\rho_e h_e$ is the overall electrode areal mass and $\rho_q h_q$ is the quartz substrate mass.

2. The sensing device of claim 1, wherein the piezoelectric resonating material is AT-cut quartz.

3. The sensing device of claim 2, wherein the AT-cut crystals has an operating frequency of 5 MHz or 11 MHz.

4. The sensing device of claim 2, wherein the AT-cut quartz is polished with a 1-inch diameter.

5. The sensing device of claim 4, wherein the AT-cut quarts has an angle of 35° with a one-minute precision.

6. The sensing device of claim 1, wherein the electrodes are further comprised of chromium adhesion and gold layers.

7. The sensing device of claim 6, wherein the chromium adhesion layer is about 75 angstroms and the gold layer is about 1050 angstroms.

8. The sensing device of claim 6, wherein the chromium layer is 75±10 Å thick and the gold layer is 1050±10 Å thick.

9. The sensing device of claim 1, further comprising hydrophobic alkanethiol self assembled monolayer disposed on the first face of the piezoelectric resonating material.

10. A sensing device, comprising:
a nanobalance/calorimeter, further comprising:
   a calorimeter body;
   a heat sink in thermal communication with the calorimeter body;
   at least one input on the calorimeter body;
a TSM sensing device, further comprising:
   a piezoelectric resonating material having a first face and a second face;
   a first electrode disposed on the first face, wherein the first electrode has a ring geometry further comprising an inner ring diameter of 4 mm and an outer ring diameter of 10 mm;
   a second electrode disposed on the second face, wherein the first electrode has a circular geometry further comprising an outer diameter of 10 mm;
   a polymeric layer on at least a portion of the first electrode; and
   wherein the sensing device has an electrode mass loading factor of 0.0025 to 0.0088, where $$R = \frac{\rho_e h_e}{\rho_q h_q}$$

where $\rho_e h_e$ is the overall electrode areal mass and $\rho_q h_q$ is the quartz substrate mass.

11. The sensing device of claim 10, wherein the piezoelectric resonating material is AT-cut quartz.

12. The sensing device of claim 11, wherein the AT-cut crystals has an operating frequency of 5 MHz or 11 MHz.

13. The sensing device of claim 10, wherein the second electrode further comprising an outer diameter of 10 mm.

14. The sensing device of claim 10, wherein the electrodes are further comprised of chromium adhesion and gold layers.

15. The sensing device of claim 14, wherein the chromium adhesion layer is about 75 angstroms and the gold layer is about 1050 angstroms.

16. The sensing device of claim 10, further comprising at least a micropositioner, an oscillator circuit, or a humidity controller.

17. The sensing device of claim 10, wherein the nanobalance/calorimeter further comprises an inert gas source, in fluid communication with the calorimeter such that the inert gas source may be injected into the calorimeter.

18. The sensing device of claim 10, wherein the TSM sensing device is thermally coupled to a heat sink through a Peltier thermocouple plate.

19. The sensing device of claim 10, wherein the calorimeter is adapted to operate between ambient temperature and 100° C.

20. The sensing device of claim 10, further comprising channels drilled in the body, adapted to permit water circulation throughout the body.

* * * * *